(12) United States Patent
Shao et al.

(10) Patent No.: US 12,304,882 B2
(45) Date of Patent: May 20, 2025

(54) PREGABALIN ARTIFICIAL HAPTEN, ARTIFICIAL ANTIGEN AND PREPARATION METHOD THEREFOR AND APPLICATION THEREOF

(71) Applicant: HANGZHOU TONGZHOU BIOTECHNOLOGY CO., LTD., Zhejiang Province (CN)

(72) Inventors: Yueshui Shao, Zhejiang Province (CN); Zhen Wang, Zhejiang Province (CN)

(73) Assignee: HANGZHOU TONGZHOU BIOTECHNOLOGY CO., LTD., Hangzhou (CN)

( * ) Notice: Subject to any disclaimer, the term of this patent is extended or adjusted under 35 U.S.C. 154(b) by 19 days.

(21) Appl. No.: 18/405,102

(22) Filed: Jan. 5, 2024

(65) Prior Publication Data
US 2024/0174600 A1    May 30, 2024

Related U.S. Application Data

(62) Division of application No. 17/398,841, filed on Aug. 10, 2021, now Pat. No. 11,897,831.

(30) Foreign Application Priority Data

Mar. 11, 2021 (CN) .......................... 202110263513.1

(51) Int. Cl.
*C07C 235/76* (2006.01)
*C07C 231/14* (2006.01)
*C07K 16/44* (2006.01)
*G01N 33/94* (2006.01)

(52) U.S. Cl.
CPC .......... *C07C 235/76* (2013.01); *C07C 231/14* (2013.01); *C07K 16/44* (2013.01); *G01N 33/9473* (2013.01)

(58) Field of Classification Search
CPC .......................... G01N 33/9473; C07C 235/76; C07C 231/14; C07K 16/44
See application file for complete search history.

(56) References Cited

FOREIGN PATENT DOCUMENTS

EP    3067700 A1    9/2016

OTHER PUBLICATIONS

Thompson, S. (2004). Small-Molecule-Protein Conjugattion Procedures, In. Decler, J., Reischl, U., (eds), Molecular Diagnosis of Infectious Diseases, Methods in Molecular Medicine, vol. 94, Humana Press. https:/doi.org/10.1385, 1-59259-679-7:255 (Year: 2004).

Stech, M., et al., "Cell-Free synthesis of functional antibodies using a coupled in vitro transcription-translation system based on CHO cell lysates." Scientific reports 7.1 (2017): 12030. (Year:2017).

*Primary Examiner* — Robert J Yamasaki
*Assistant Examiner* — Trevor Kane
(74) *Attorney, Agent, or Firm* — Muncy, Geissler, Olds & Lowe, P.C.

(57) ABSTRACT

Disclosed are a pregabalin artificial hapten, artificial antigen and preparation method therefor and application thereof. The structure of the pregabalin artificial hapten is shown as formula (I) and structure of the pregabalin artificial antigen is shown as formula (II). The application is in the preparation for anti-pregabalin antibodies with the pregabalin artificial antigen. The pregabalin artificial hapten retains the characteristic structure of pregabalin to the greatest extent, and has an active group that can be coupled with a carrier protein, and can be used as an antigenic determinant; the pregabalin artificial antigen obtained by further preparation can immune to obtain anti-pregabalin antibodies with high affinity, high sensitivity and strong specificity. The titer of the immune serum obtained by immunizing New Zealand white rabbits is as high as 1:90000, which can be used for rapid and accurate immunoassay of pregabalin.

4 Claims, 16 Drawing Sheets

PREGABALIN ARTIFICIAL HAPTEN, ARTIFICIAL ANTIGEN AND PREPARATION METHOD THEREFOR AND APPLICATION THEREOF

CROSS-REFERENCE TO RELATED APPLICATION

This is a divisional application of application Ser. No. 17/398,841, filed on Aug. 10, 2021, which relies on, for priority, China Patent Application No. 2021102635131 entitled "PREGABALIN ARTIFICIAL HAPTEN, ARTIFICIAL ANTIGEN AND PREPARATION METHOD THEREFOR AND APPLICATION THEREOF", filed on Mar. 11, 2021, the disclosures of which are herein incorporated by reference in its entirety.

FIELD OF THE INVENTION

The present invention relates to the field of biotechnology, and more specifically relates to a pregabalin artificial hapten, artificial antigen and preparation method therefor and application thereof.

BACKGROUND

As an anticonvulsant medication, pregabalin is mainly used in the treatment of partial seizures in adult epilepsy, diabetic neuroplasia, postherpetic neuralgia and anxiety disorders. It is a GABA analogue, which can reduce the release of neurotransmitters such as glutamate, norepinephrine, substance P and calcitonin gene-related peptides. Recent studies have found that it can also play a role in the treatment of addiction to tobacco, alcohol and benzodiazepines.

Although the current reports of pregabalin abuse are very rare, it is still necessary to pay attention to patients with substance dependence.

It is prone to drug abuse symptoms if people take the pregabalin beyond the recommended dose or use a wrong medication (such as rectal administration or intranasal administration). Skopp et al. once reported a case of abnormal agitation, anxiety attacks, and abnormal thinking after abuse of pregabalin. At present, there is no specific antidote for the abuse of pregabalin, and insomnia, nausea, headache, diarrhea and other discomforts may occur after rapid withdrawal. Therefore, there is an urgent need for establishing rapid, sensitive, and accurate detection technology.

At present, the detection of pregabalin mainly relies on high performance liquid chromatography (HPLC), gas chromatography (GC), thin layer chromatography (TLC), mass spectrometry (MS), etc., but the instrument is expensive, and the detection is time-consuming, and It requires professional and technical personnel to operate, and cannot meet the requirements of modern detection for fast and accurate.

Immunoassays can make up for all the above shortcomings. The immunoassay method is an analytical method for detecting various substances (drugs, hormones, proteins, microorganisms, etc.) using the specific binding reaction of antigen and antibody. The key to establishing an immunoassay method for small molecule compounds is capable of producing antibodies having high affinity and high specificity for small molecule compounds. However, because most small molecular compounds (molecular weight less than 1000) including pregabalin, have no immunogenicity, i.e., lack of T cell epitope and cannot directly induce animal bodies to produce specific antibodies, so small molecular substances are called for hapten. By appropriate chemical modification, a linker with its end having active group is connected to a certain position of the hapten molecular structure, and then bonded to a macromolecular carrier, to form a hapten-carrier conjugate (i.e. artificial antigen), the artificial antigen can indirectly induce proliferation and differentiation of B cells by means of T cell epitopes, and then produce specific antibodies.

SUMMARY OF THE INVENTION

The present invention provides a pregabalin artificial hapten that retains the characteristic structure of pregabalin to the greatest extent, and has an active group capable of coupling to a carrier protein, which can be used as an antigenic determination cluster.

A pregabalin artificial hapten, having a molecular structure formula as shown in (I):

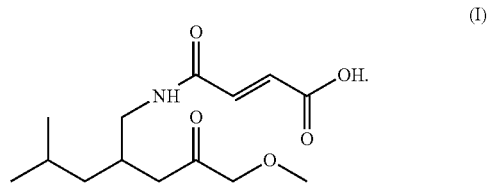 [SMILES: COCC(=O)CC(CNC(=O)/C=C/C(=O)O)CC(C)C]

The present invention also provides the preparation method of the pregabalin artificial hapten, including the following steps:
(1) dissolving pregabalin in methanol, adding concentrated sulfuric acid, stirring for reaction while refluxing at 68° C. for 24 hours, neutralizing the reaction product in sodium hydrogen carbonate solid, drying, then extracting with tetrahydrofuran to obtain a yellowish oily product A.
(2) mixing the yellowish oily product A with maleic anhydride in the molar ratio of 1:2~3 in dichloromethane, adding 4-dimethylaminopyridine, and allowing the reaction at room temperature for 20 hours with stirring, washing the reaction product by purified water, taking organic phase, drying and filtering to get a brownish-yellow oily product;
separating the above-mentioned brownish-yellow yellow oily product from a thin layer chromatography (TLC) to obtain a light yellow oily product, that is, the pregabalin artificial hapten I; the molar ratio of the TLC chromatography solution is 95% ethanol:dichloromethane:1,4-dioxane:ammonia water=8:10:1:1, and the product $R_f$=0.4.

Through the above method, a linker is introduced at the N position of pregabalin, and the introduction of the linker at the modified site can retain the characteristic structure of pregabalin to the greatest extent.

Compared with the use of general saturated chain hydrocarbons as the linker, the linker used in the present invention contains a conjugated double bond structure, which makes the hapten possess ultraviolet absorption characteristics, and not only can make the general colorless under 254 nm light wave pregabalin becomes a pregabalin artificial hapten that develops under the light wave, which greatly reduces the difficulty of purifying the artificial hapten; and can increase the specificity of the artificial hapten, maintain conformational stability in the solution, and improve the immune characteristics of the artificial antigen II obtained.

The present invention also provides a pregabalin artificial antigen, the molecular structure of which is shown in (II):

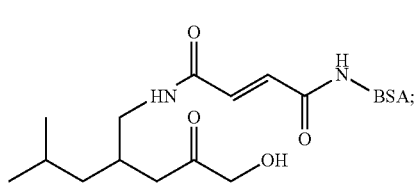

(II)

wherein BSA is bovine serum albumin.

The present invention also provides a method for preparing the pregabalin artificial antigen, which comprises: binding the pregabalin artificial hapten II with bovine serum albumin by the active ester method to obtain the pregabalin artificial antigen II. Specifically, it includes the following steps:
 (a) Dissolving the pregabalin artificial hapten I, N-hydroxysuccinimide, and dicyclohexylcarbodiimide in a molar ratio of 1:1.35~1.5:1.35~1.5 in N,N-Dimethylformamide, stirring for reaction at room temperature for 18 hours; after the reaction, collecting the supernatant by centrifugation;
 (b) Adding the supernatant dropwise to the bovine serum albumin solution, allowing the reaction mixture to stand at 4° C. overnight, dialyzing with 0.5% sodium carbonate aqueous solution and phosphate buffer solution (PBS) at pH=12.00, and centrifuging to obtain the supernatant solution to obtain pregabalin artificial antigen II.

The bovine serum albumin solution in the present invention is prepared by dissolving bovine serum albumin in a phosphate buffer with a phosphate ion concentration of 0.01 mol/L and a pH of 7.2 to 7.4.

In step (b), the concentration of the bovine serum albumin solution is 20 mg/ml, and the volume ratio of the supernatant to the bovine serum albumin solution is 1:5.

The bovine serum albumin (BSA) selected in the present invention as a macromolecular carrier has the following advantages compared with other carrier proteins: ①BSA has 583 amino acid residues, which is easier to couple with pregabalin hapten, and pregabalin artificial antigens with different coupling ratios and high immunogenicity can be prepared; ②BSA is economical and low-cost; ③BSA is chemically stable, and has good solubility and stability in acidic and weakly alkaline environments, suitable for long-term storage.

The invention also provides the application of the pregabalin artificial antigen II in the preparation of anti-pregabalin antibodies.

The present invention also provides an anti-pregabalin antibody, which is a globulin having specific immunity response to pregabalin obtained by immunizing animals with the pregabalin artificial antigen of claim 3

The present invention also provides the application of the anti-pregabalin antibody in detecting pregabalin.

The experiment finds that the titer of the immune serum obtained by immunizing New Zealand white rabbits with the pregabalin artificial antigen is 1:90000. It shows that the pregabalin artificial antigen of the present invention can immune to obtain an anti-pregabalin antibody with high affinity, high sensitivity and strong specificity, and the anti-pregabalin antibody can be used for immunodetection and analysis of pregabalin.

Compared with the prior art, the present invention has the following beneficial effects:

The pregabalin artificial hapten of the present invention retains the characteristic structure of pregabalin to the greatest extent, and has an active group that can be coupled with a carrier protein, and can be used as an antigenic determinant; the pregabalin artificial antigen obtained by further preparation can immune to obtain anti-pregabalin antibodies with high affinity, high sensitivity and strong specificity. The titer of the immune serum obtained by immunizing New Zealand white rabbits is as high as 1:90000, which can be used for rapid and accurate immunoassay of pregabalin.

Figure 2:
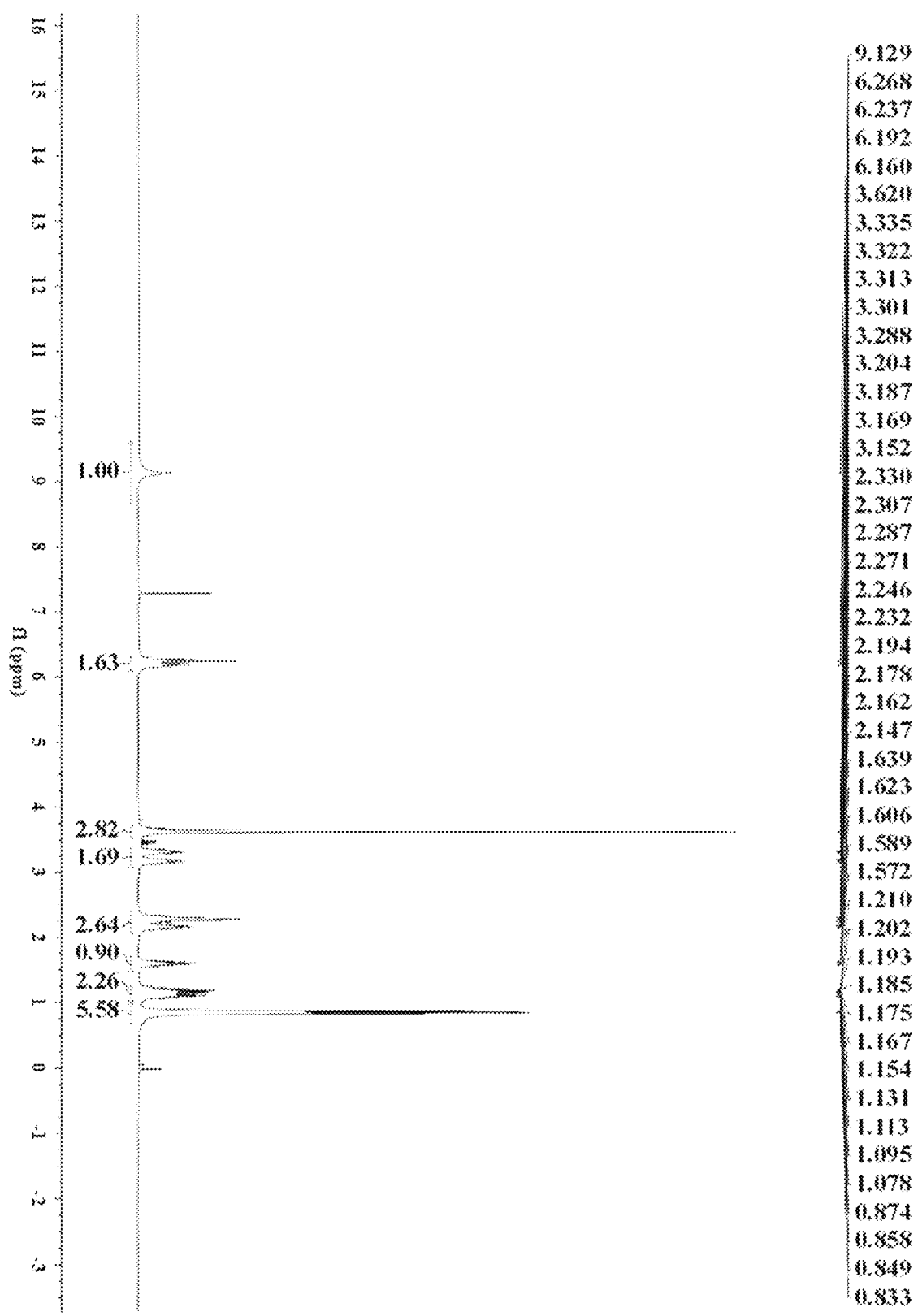
Figure 3:
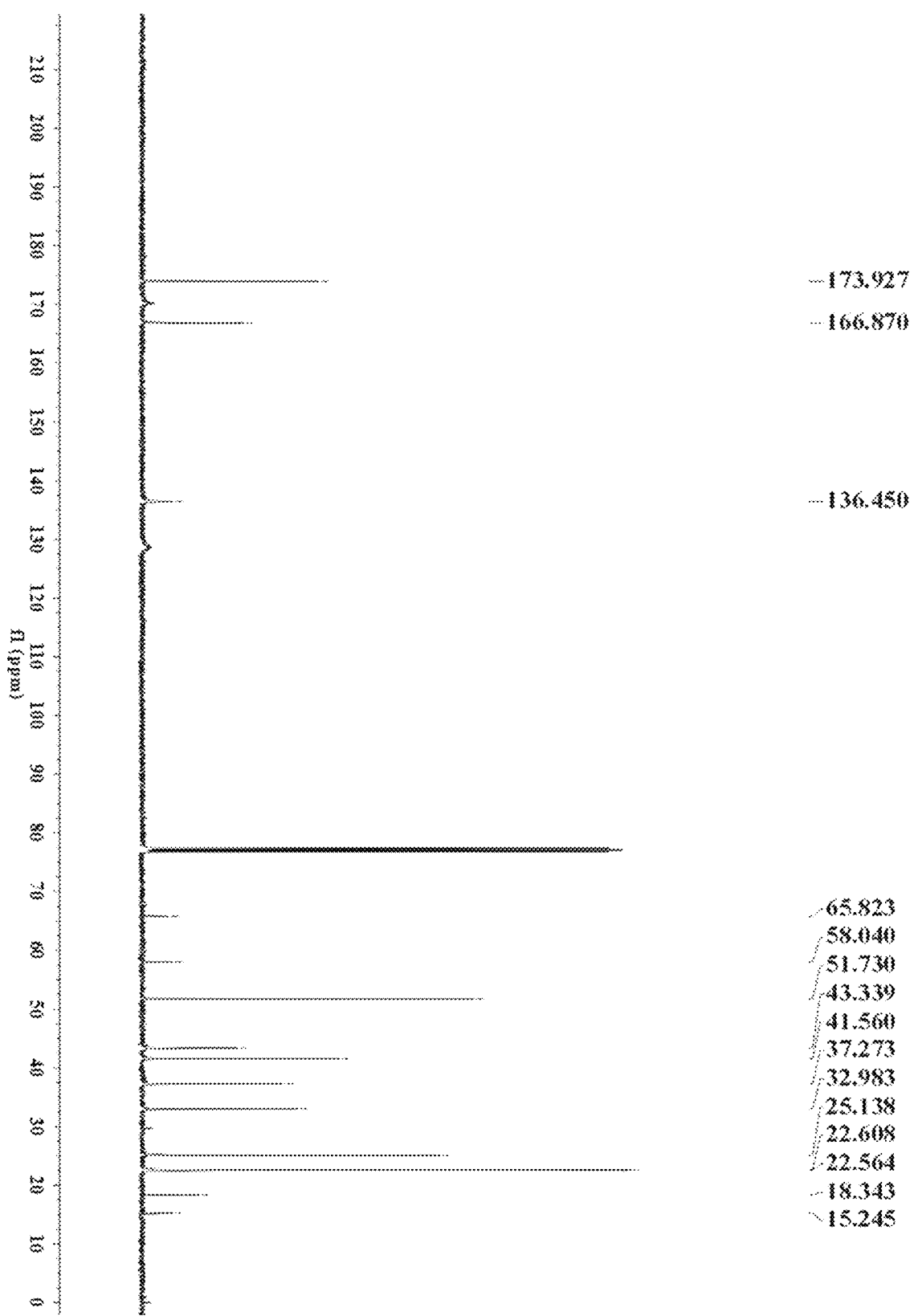
Figure 4:
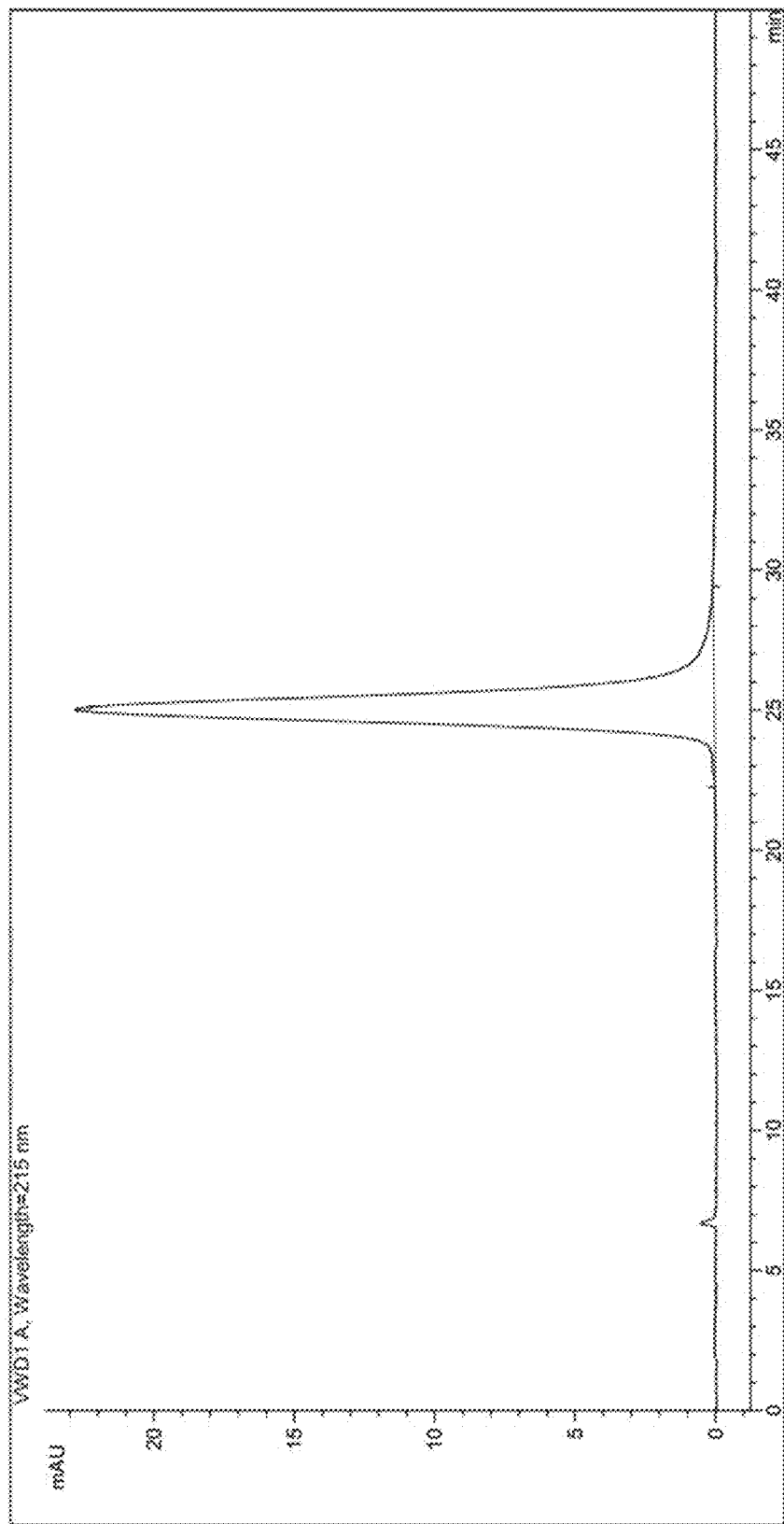
Figure 5:
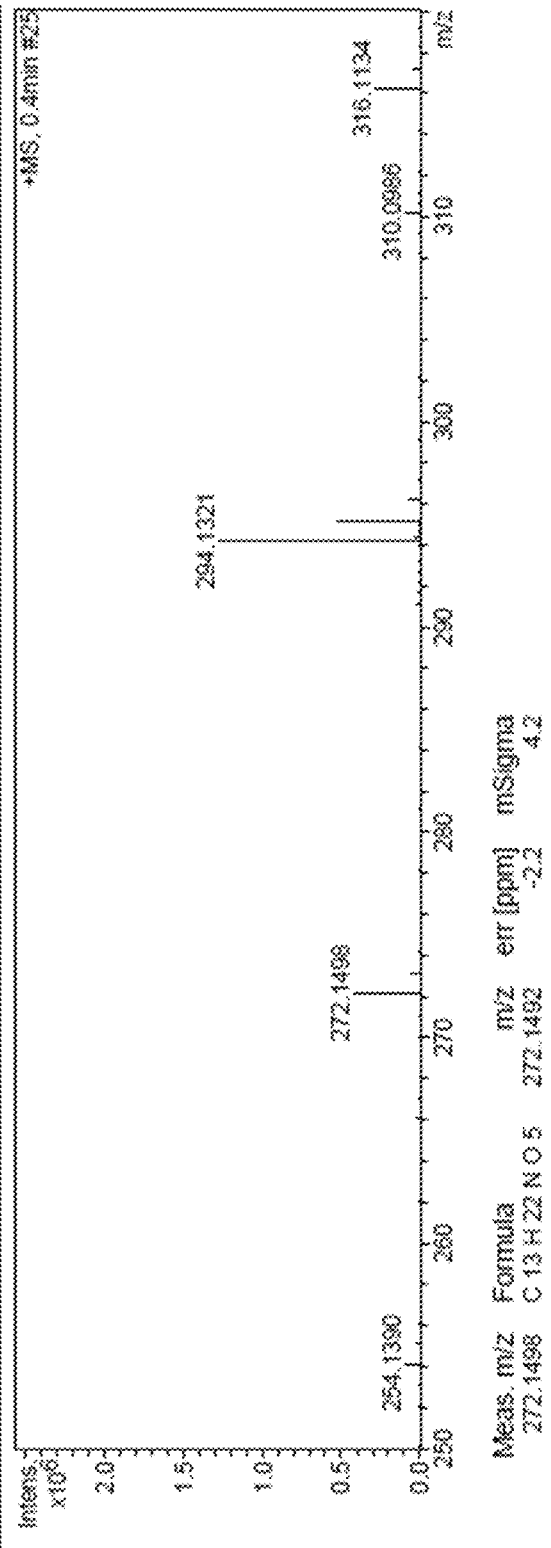
Figure 6:
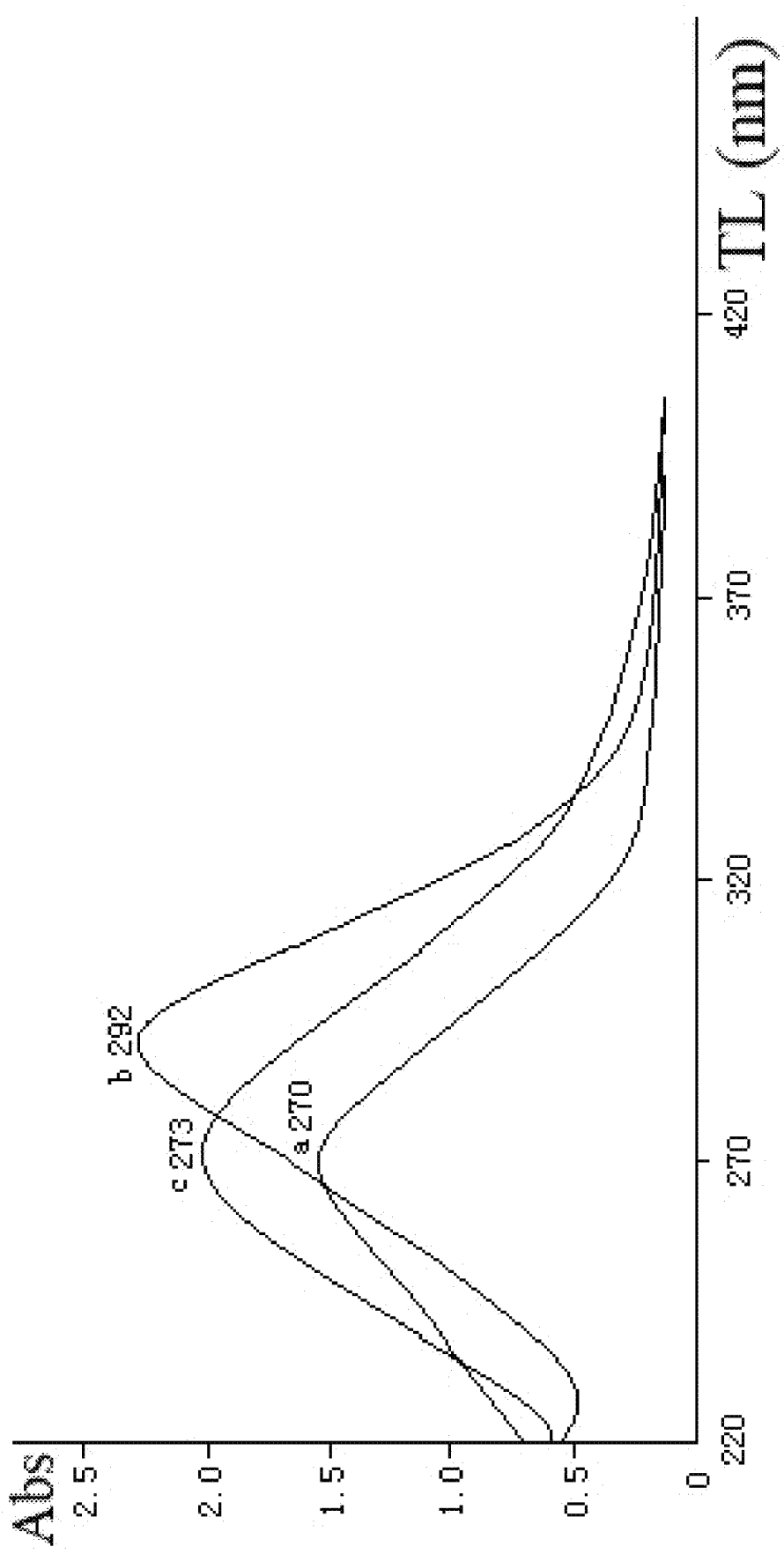
Figure 7:
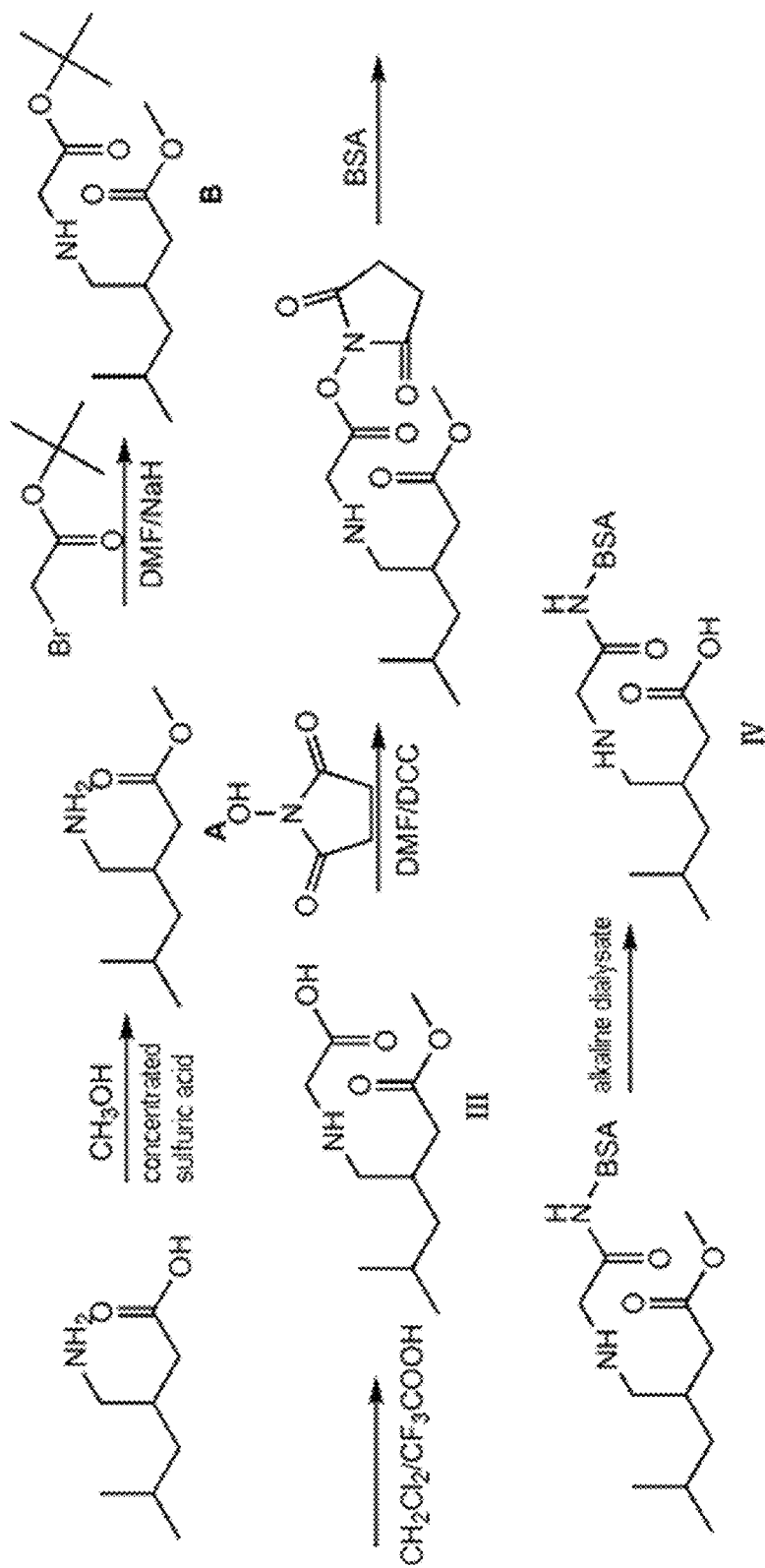
Figure 8:
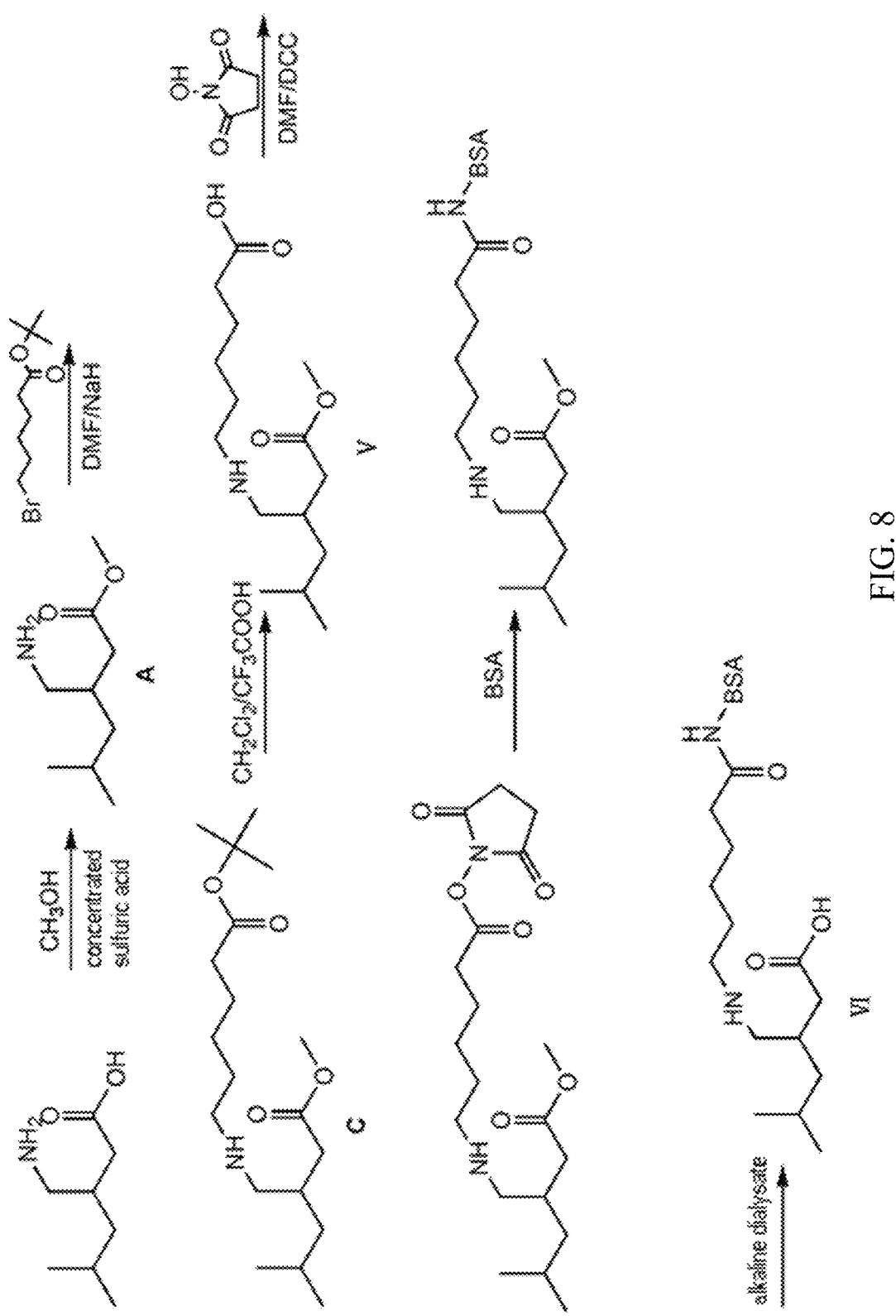
Figure 9:
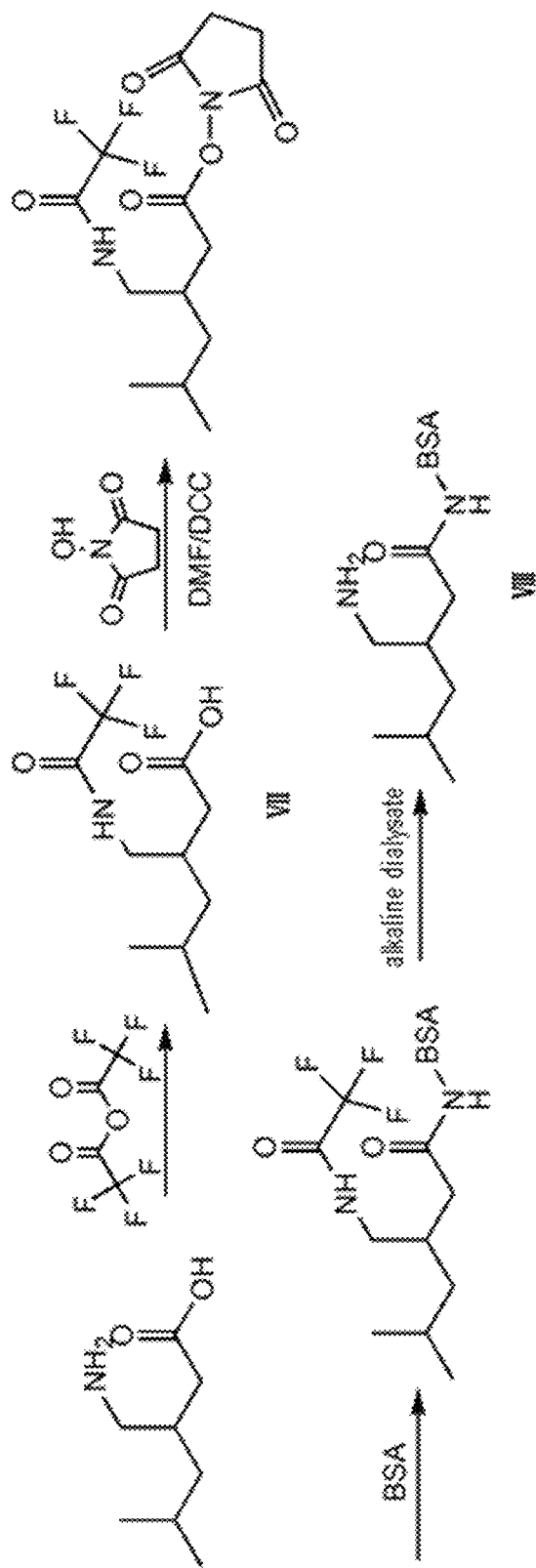
Figure 10:
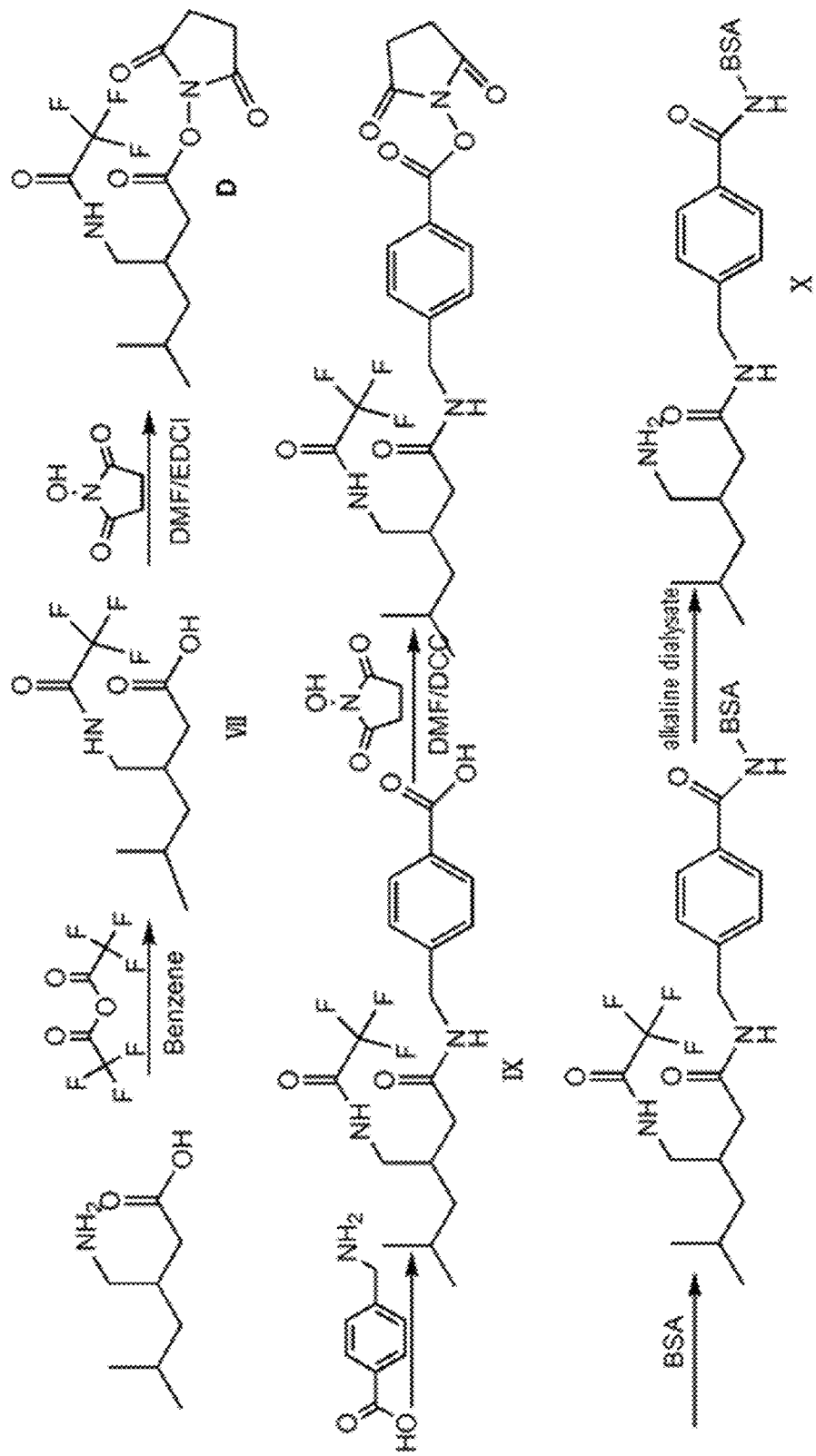
Figure 11:
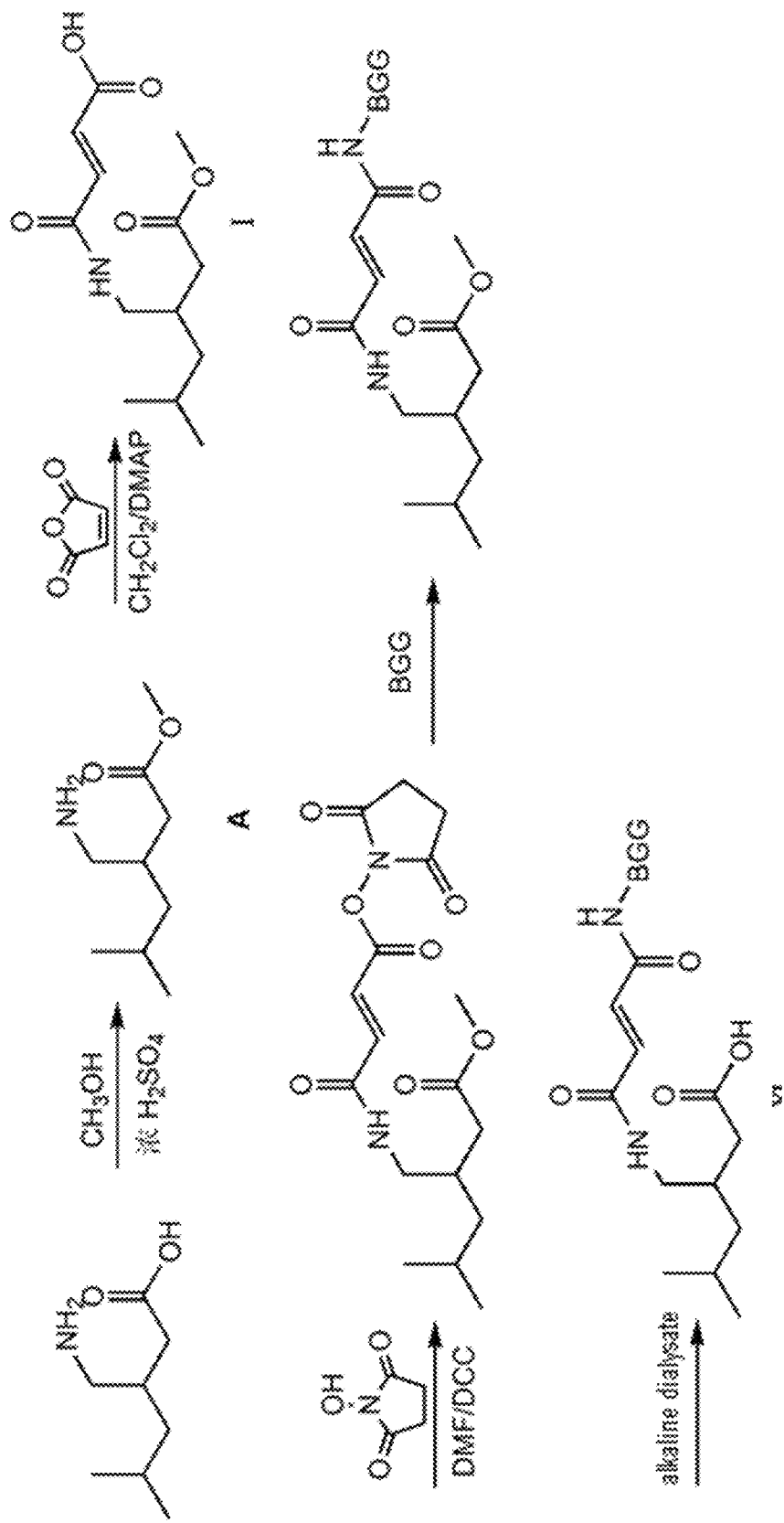
Figure 12:
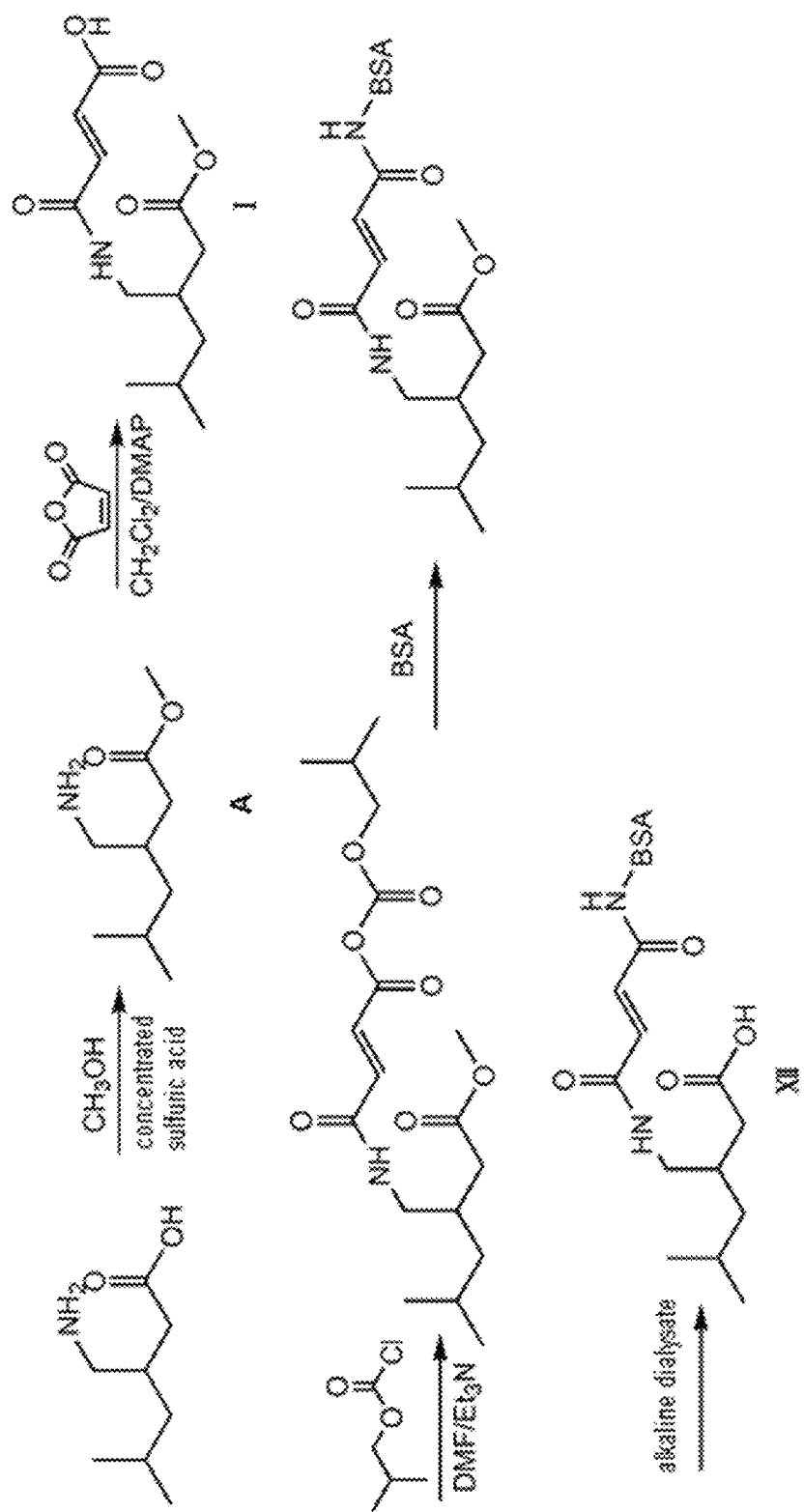
Figure 13:
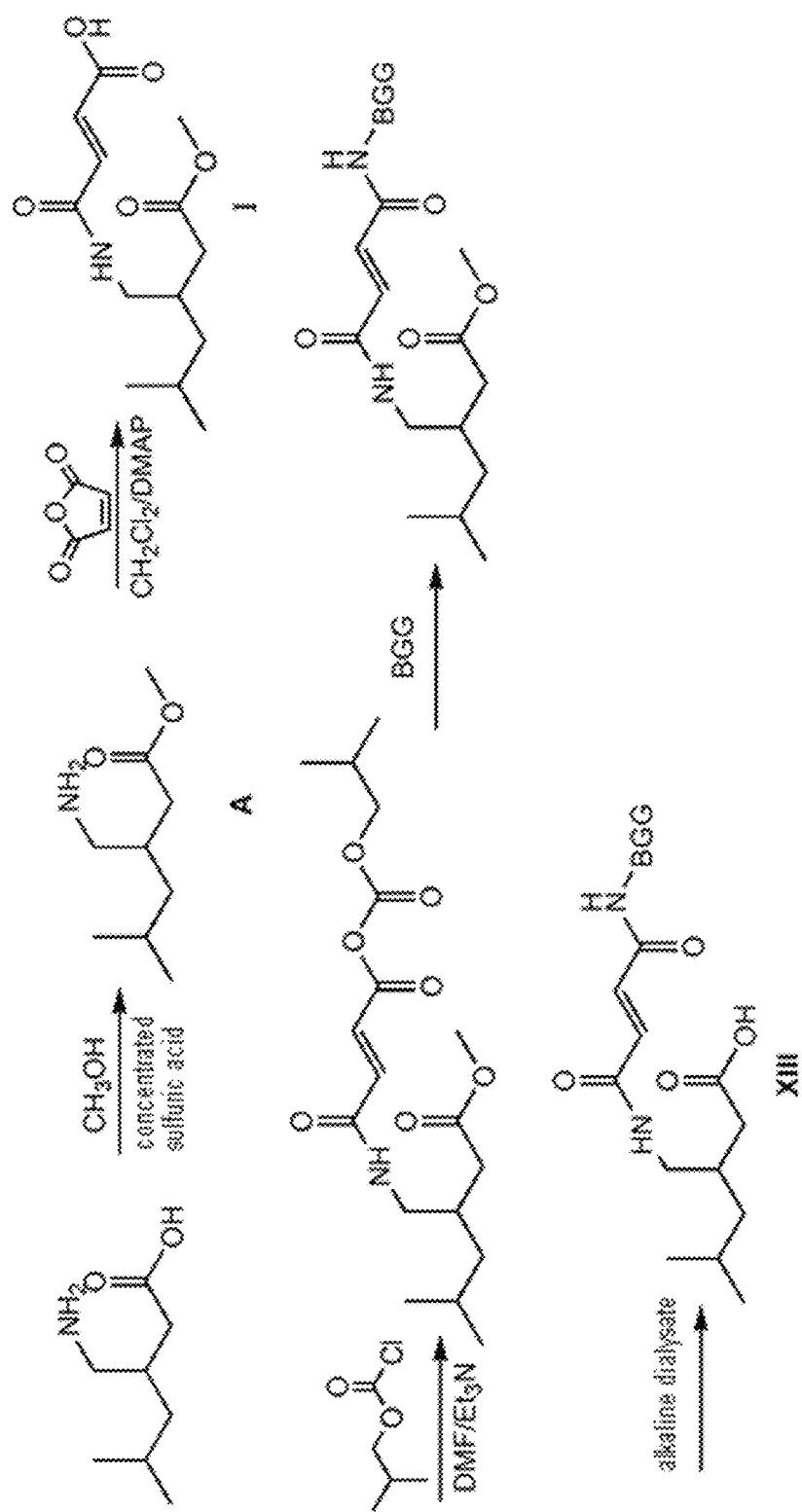
Figure 14:
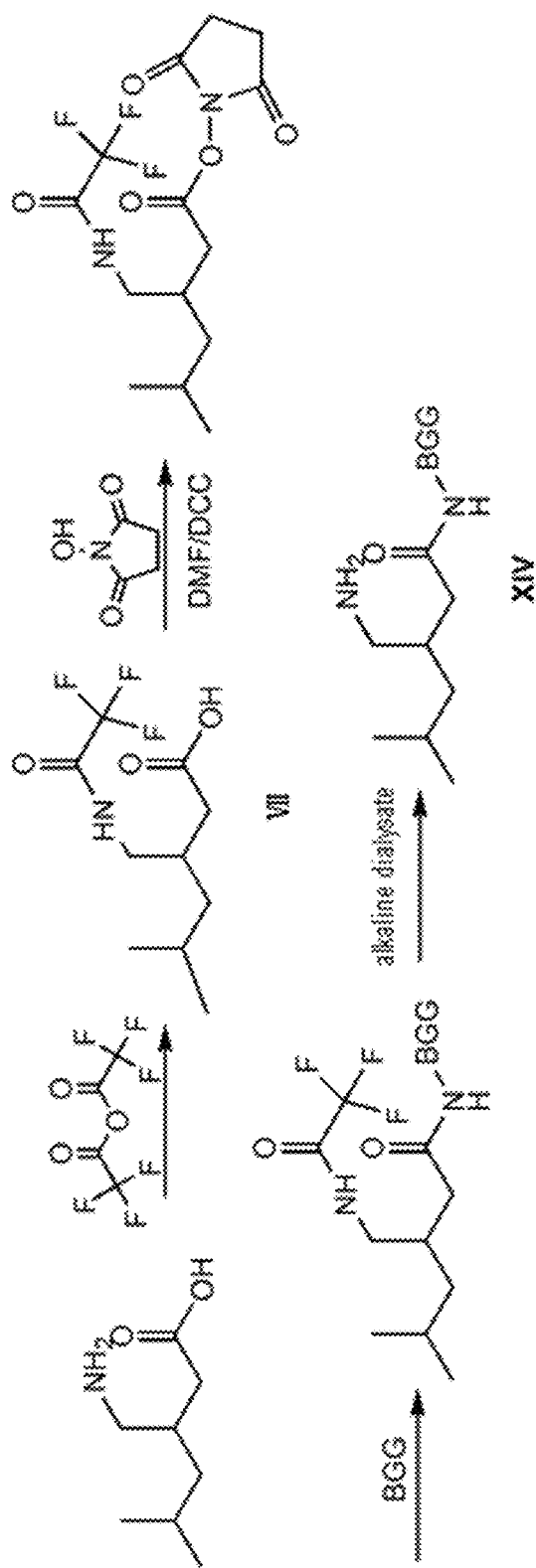
Figure 15:
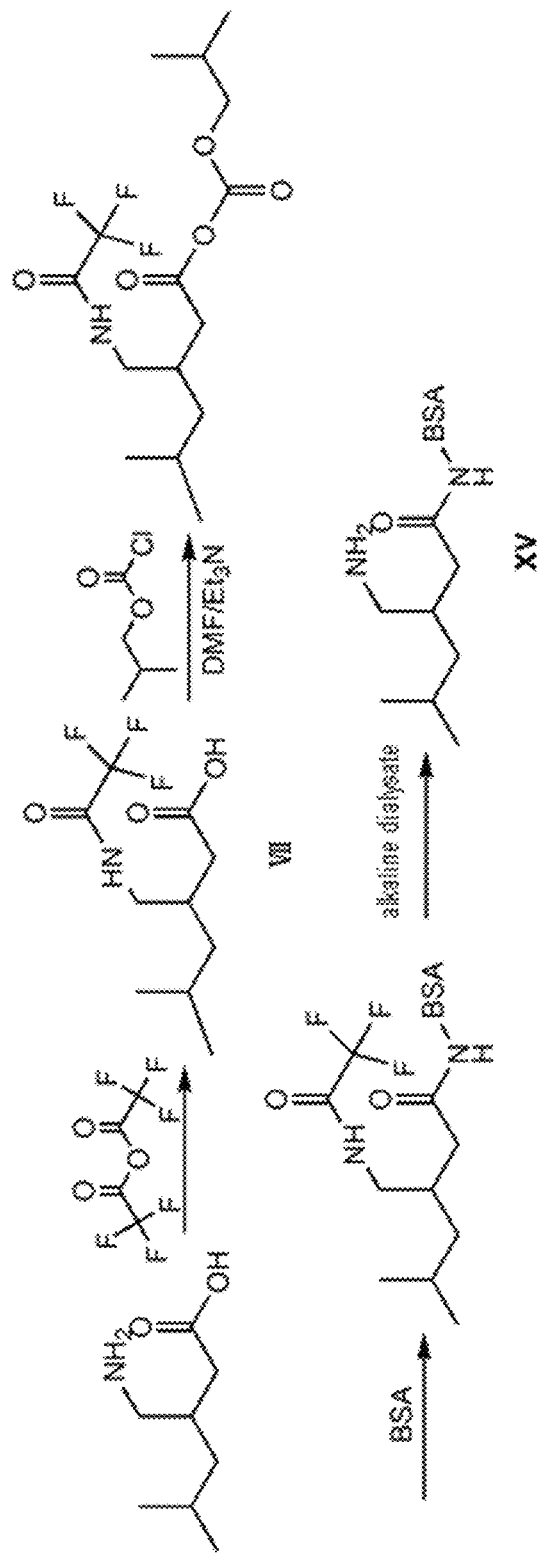
Figure 16:
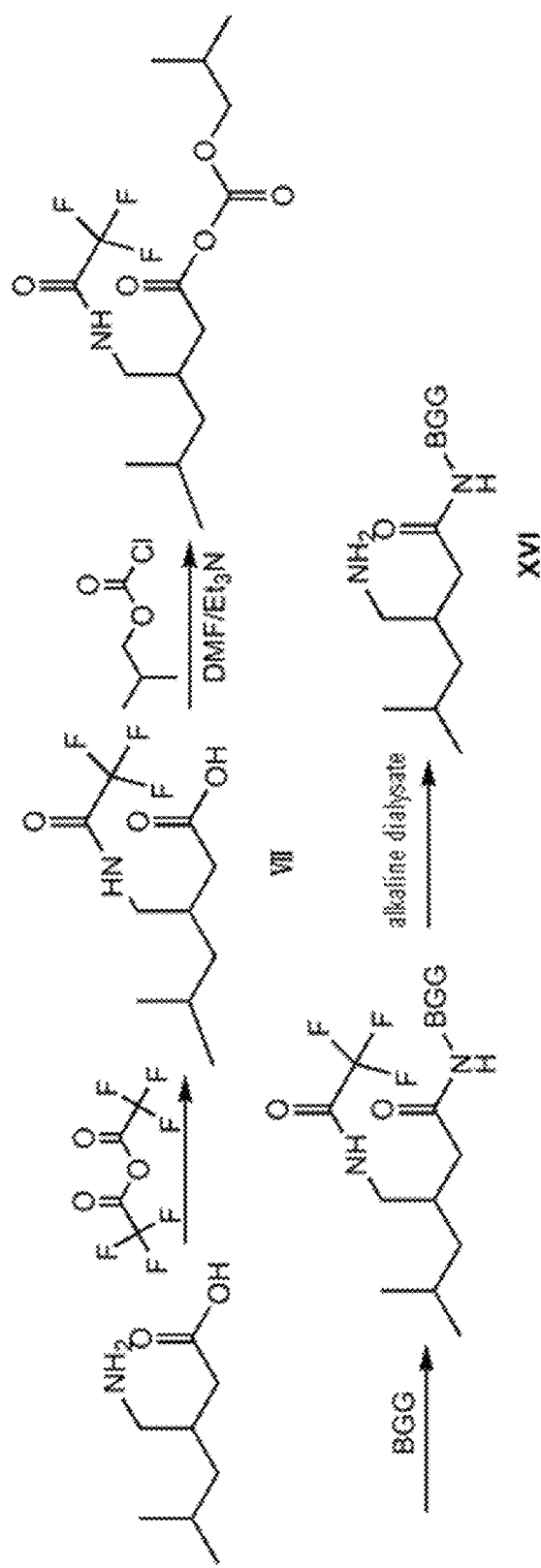

Among them, DMAP stands for 4-dimethylaminopyridine, NHS stands for N-hydroxysuccinimide, DCC stands for dicyclohexylcarbodiimide, BSA stands for bovine serum albumin, and DMF stands for N,N-dimethylformamide. Similarly hereinafter;

FIG. 2 is a hydrogen NMR spectrum of the pregabalin artificial hapten;

FIG. 3 is a carbon NMR spectrum of the pregabalin artificial hapten;

FIG. 4 is a liquid chromatogram of pregabalin artificial hapten;

among them, mAU means milli-absorbance unit, min means minute;

FIG. 5 is a mass spectrum of pregabalin hapten;

FIG. 6 is a UV scan of bovine serum albumin, pregabalin artificial hapten, and pregabalin artificial antigen;

among them, Abs means ultraviolet-visible absorption spectrum, WL (nm) means wavelength (nm);

FIG. 7 is a flow chart of the preparation of pregabalin artificial antigen according to Comparative Example 1;

FIG. 8 is a flow chart of the preparation of pregabalin artificial antigen according to Comparative Example 2;

FIG. 9 is a flow chart of the preparation of pregabalin artificial antigen according to Comparative Example 3;

FIG. 10 is a flow chart of the preparation of pregabalin artificial antigen according to Comparative Example 4;

wherein, EDCI means 1-(3-dimethylaminopropyl)-3-ethylcarbodiimide hydrochloride, the same below;

FIG. 11 is a flow chart of the preparation of pregabalin artificial antigen according to Comparative Example 5;

wherein, BGG stands for bovine gamma globulin;

FIG. 12 is a flow chart of the preparation of pregabalin artificial antigen according to Comparative Example 6;

FIG. 13 is a flow chart of the preparation of pregabalin artificial antigen according to Comparative Example 7;

FIG. 14 is a flow chart of the preparation of pregabalin artificial antigen according to Comparative Example 8;

FIG. 15 is a flow chart of the preparation of pregabalin artificial antigen according to Comparative Example 9;

wherein, EDCI means 1-(3-dimethylaminopropyl)-3-ethylcarbodiimide hydrochloride, the same below;

FIG. 16 is a flow chart of the preparation of pregabalin artificial antigen according to Comparative Example 10;

DETAINED DESCRIPTION OF THE INVENTION

Embodiment 1

Figure 1:
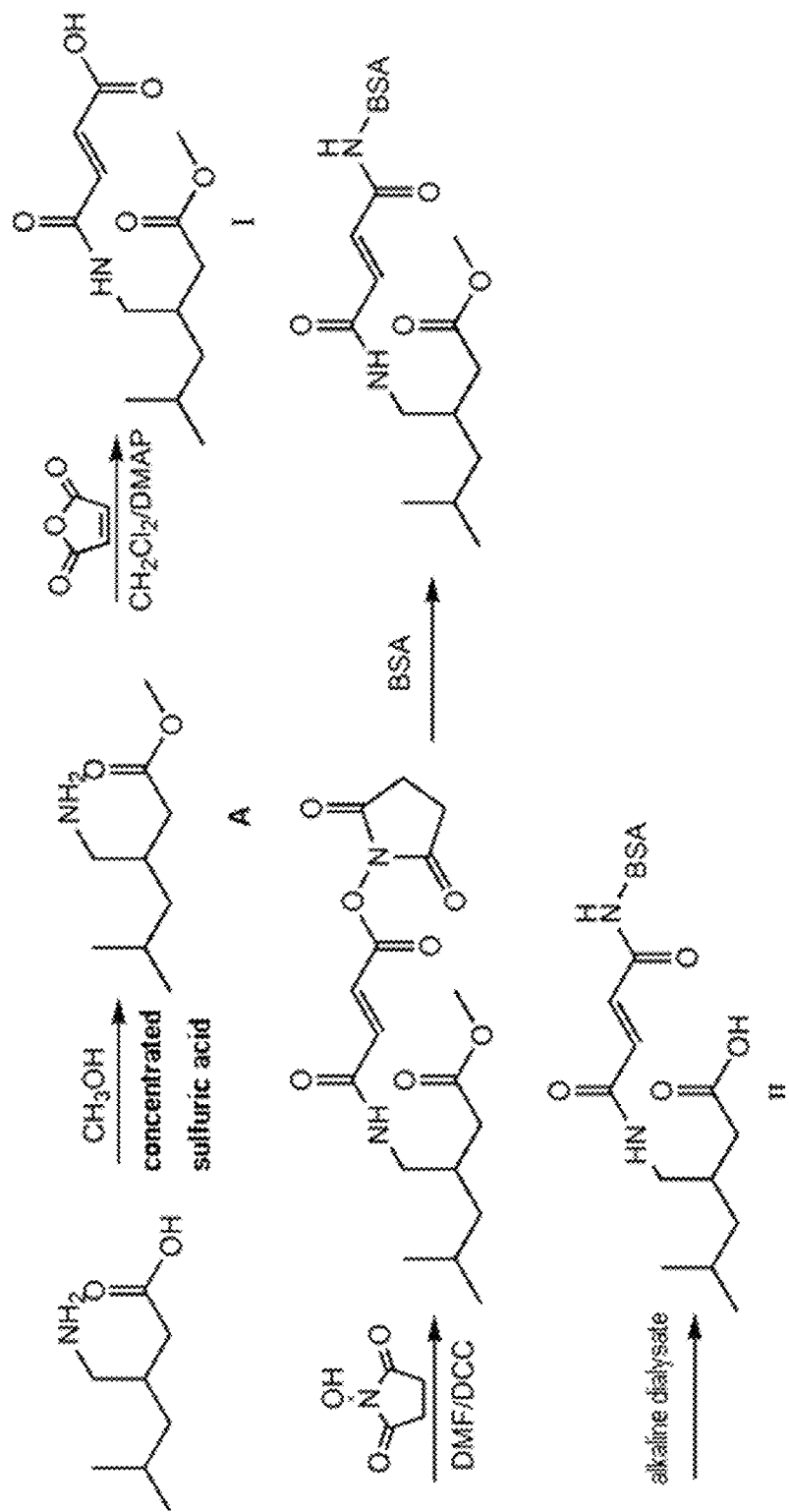
FIG. 1 is a flow chart of the preparation of pregabalin artificial antigen according to the present invention.

The method for preparing pregabalin artificial antigen in the embodiment of the present invention (the reaction process is shown in FIG. 1) includes the following steps:

(1) Preparation of artificial hapten:

①  200 mg (1.258 mmol) of pregabalin was weighed and put into a 50 ml single-necked round bottom flask; 10 ml methanol and 0.5 ml concentrated sulfuric acid was added in with a stir bar, and the reaction flask was placed into an oil bath at 68° ° C. with stirring and reflux for 24 hours; after the reaction was complete, they were cooled to room temperature, and NaHCO₃ solid was slowly added to the reaction system to adjust the pH to 7-8, the residue was evaporated under reduced pressure, and then was extracted with 15 ml of tetrahydrofuran, filtered and rotationally dried to obtain 210 mg (1.214 mmol) of yellowish oily product A;

② In a 50 ml single-necked round bottom flask, 210 mg (1.214 mmol) of yellowish oily product A of step ① was dissolved in 10 ml of dichloromethane, 238 mg (2.428 mmol) of maleic anhydride and 20 mg of 4-dimethyl-aminopyridine (DMAP) was added, stirring for reaction at room temperature for 20 hours; after the reaction was over, the reaction solution was transferred to a 60 ml separatory funnel, washed twice with 15 ml purified water, the organic phase was dried over anhydrous magnesium sulfate, filtered, and then rotationally dried. 160 mg of crude product was obtained as a brownish-yellow oily product.

The crude product was separated by thin-layer chromatography (TLC), the solvent and eluent were absolute ethanol, and the molar ratio of the TLC chromatography solution was 95% ethanol:dichloromethane:1,4-dioxane:ammonia water=8:10:1:1, and the points with $R_f$=0.4 were collected, then eluted with 150 ml absolute ethanol, filtered and concentrated to obtain 72 mg (0.266 mmol) of light yellow oily product, namely pregabalin artificial hapten I.

The hydrogen nuclear magnetic resonance spectrum of pregabalin artificial hapten was shown in FIG. 2, and the carbon nuclear magnetic resonance spectrum ws shown in FIG. 3.

The NMR data of pregabalin artificial hapten were:

$^1$H NMR (400 MHZ, Chloroform-d) δ 9.13 (s, 1H), 6.27-6.19 (m, 2H), 3.62 (s, 3H), 3.35-3.14 (m, 2H), 2.37-2.11 (m, 3H), 1.60 (dq, J=13.2, 6.4 Hz, 1H), 1.23-1.06 (m, 2H), 0.85 (dd, J=10, 6.4 Hz, 6H).

$^{13}$C NMR (101 MHz, Chloroform-d) δ 173.93, 166.87, 136.45, 65.82, 58.04, 51.73, 43.34, 41.56, 37.27, 32.98, 25.14, 22.61, 22.56, 18.34, 15.24.

The compound inferred based on the proton nuclear magnetic resonance spectrum and carbon nuclear magnetic resonance spectrum data was basically consistent with the pregabalin artificial hapten.

The liquid chromatogram of pregabalin artificial hapten was shown in FIG. 4 (UV detector, wavelength 215 nm), and the mass spectrum of pregabalin hapten was shown in FIG. 5.

It can be seen from FIG. 4 that the purity of the purified pregabalin artificial hapten was more than 99.9%. From FIG. 5, it can be seen that the main mass-to-charge ratio (m/z) of the molecular ion peak of the pregabalin artificial hapten obtained in this embodiment are 272.1498 (M+H), 294.1321 (M+Na) and 310.0986 (M+K), which are consistent with their theoretical molecular weight of 271.14. Combined with nuclear magnetic resonance data, it can be determined that the final compound obtained in step ② is the pregabalin artificial hapten I.

(2) Preparation of pregabalin artificial antigen:

③ 72 mg (0.266 mmol) of pregabalin artificial hapten was placed in a 50 ml round-bottomed flask added with a stir bar, 3.6 ml of N,N-dimethylformamide (DMF) was added to dissolve, and then 46 mg (0.400 mmol) of N-Hydroxysuccinimide (NHS) and 82 mg (0.398 mmol) of dicyclohexylcarbodiimide (DCC) were added, stirring for reaction at 25° C. for 18 hours, centrifuged after the reaction, and the supernatant was taken for use.

④ 14.500 g (0.0405 mol) of disodium hydrogen phosphate dodecahydrate, 43.875 g (0.75 mol) of sodium chloride, and 1.495 g (0.00958 mol) of sodium dihydrogen phosphate dehydrate were weighed and dissolved with double distilled water and the volume was diluted to 5.0 L to obtain phosphate buffer solution (PBS) with a phosphate ion concentration of 0.01 mol/L and a sodium ion concentration of 0.17 mol/L.

⑤ 25 g of Na₂CO₃ solid powder was dissolved in purified water and the volume was diluted to 5 L, and the pH was adjusted to 12.00±0.01 with 2N NaOH aqueous solution to prepare an alkaline dialysate.

⑥ 0.360 g of bovine serum albumin was weighed and dissolved in 18 ml of PBS in step ④ to obtain a bovine serum albumin solution with a concentration of 20 mg/ml.

⑦ Under rapid stirring, the supernatant of step ③ was slowly dropped into the bovine serum albumin solution of the previous step. The volume ratio of the supernatant to the bovine serum albumin solution was 1:5, and the resulting mixture was left to stand overnight at 4° C. to obtain an artificial antigen mixture.

⑧ The artificial antigen mixture from the previous step was transferred to the dialysis bag, dialyzed with the alkaline dialysis solution of step ⑤ for two days, once a day, and then the dialysis bag was transferred to the PBS buffer obtained in ④ for 7 times of dialyses, every two time intervals were not less than two hours. After the dialyses was completed, the supernatant was centrifuged to obtain the artificial antigen: pregabalin-bovine serum protein conjugate (such as formula II). FIG. 6 shows the UV scans before and after the preparation of pregabalin artificial antigen.

In FIG. 6, curve a was the UV scan of the pregabalin artificial hapten, curve b was the UV scan of the pregabalin artificial antigen, and curve c was the UV scan of the bovine serum albumin. The maximum absorption wavelength of pregabalin artificial hapten was 270 nm, and the maximum absorption wavelength of pregabalin artificial antigen was 273 nm. Compared with pregabalin hapten and bovine serum albumin, the maximum absorption wavelength of pregabalin artificial antigen had changed significantly, indicating that the pregabalin artificial hapten and bovine serum protein were successfully coupled.

Comparative Example 1

The preparation method of the pregabalin artificial antigen of this Comparative Example (the reaction process is shown in FIG. 7) includes the following steps:

(1) Preparation of pregabalin artificial hapten:

① 200 mg (1.258 mmol) of pregabalin was weighed and put into a 50 ml single-necked round-bottomed flask; 10 ml methanol and 0.5 ml concentrated sulfuric acid was added in with a stir bar, and they were placed into an oil bath at 68° C. with stirring and reflux for 24 hours; after the reaction was complete, they were cooled to room temperature, and NaHCO₃ solid was slowly added to the reaction system to adjust the pH to 7-8; the residue was evaporated under reduced pressure, and then was extracted with 15 ml of tetrahydrofuran, filtered and rotationally dried to obtain 195 mg (1.127 mmol) of yellowish oily product A;

② 195 mg (1.127 mmol) of the yellowish oily product A of step ① was dissolved in 5 ml of N,N-dimethylformamide (DMF) and placed in a 50 ml three-necked round-bottom flask. The middle mouth was connected to a condenser and dried with anhydrous CaCl2 and the left port of the tube was filled with nitrogen as a protective gas, the right port was tightly plugged with a rubber stopper, 54 mg (1.350 mmol) of NaH (60% mass fraction) solid was added from the right port, and the reaction flask was placed in a 60° C. oil bath and stirred for reaction for 30 minutes, a mixed solution of 246 μL (1.688 mmol) of tert-butyl bromoacetate and 2 ml of N,N-dimethylformamide were added dropwise with a syringe, and continued to react at 60° C. for 17 hours;

The reaction mixture was cooled to room temperature after the completion of the reaction, and transferred to a 50 ml single-necked round bottom flask with DMF, then the solvent was evaporated to dryness under reduced pressure to obtain a yellow viscous substance; then 15 ml of water was added into the flask; 15 ml*2 ethyl acetate were used to extract, the organic phases were combined, and washed with 20 ml purified water and 20 ml saturated brine separately; the organic phase was taken and dried with anhydrous $Na_2SO_4$, filtered, and then evaporated to dryness under reduced pressure to obtain 285 mg (0.993 mmol) of brownish-yellow oily substance B.

③ The 285 mg (0.993 mmol) of brownish-yellow oily substance B was dissolved in 15 ml of dichloromethane and 5 ml of trifluoroacetic acid, rapidly stirring for reaction at 25° C. for 5 hours; after the reaction was over, the solvent was evaporated under reduced pressure, then 10 ml of 10% potassium carbonate solution was added, then the aqueous phase was washed with 15 ml*3 of ethyl acetate; the aqueous phase was collected, the pH was adjusted to 3 with 6N hydrochloric acid, and then extracted with 20 ml*3 of ethyl acetate; the organic phase was collected, dried with anhydrous magnesium sulfate, filtered, and evaporated to dryness under reduced pressure to obtain a reddish-brown oil;

The reddish-brown oil was separated by TLC, the solvent and eluent were absolute ethanol, and the molar ratio of the TLC chromatography solution was 95% ethanol:dichloromethane:1,4-dioxane:ammonia water=8:10:1:1, and the points with $R_f$=0.1~0.5 were collected, eluted with 150 ml absolute ethanol, filtered and concentrated to obtain 63 mg (0.273 mmol) of brownish yellow oily product, namely pregabalin artificial hapten III.

(2) Preparation of pregabalin artificial antigen:

④ 63 mg (0.273 mmol) of pregabalin artificial hapten III was placed in a 50 ml round bottom flask, 3.15 ml of N,N-dimethylformamide (DMF) was added, and then 47 mg (0.400 mmol) of N-Hydroxysuccinimide (NHS) and 84 mg (0.409 mmol) of dicyclohexylcarbodiimide (DCC) were added, stirring for reaction at 25° C. overnight, centrifuged after the reaction, and took the supernatant for use.

⑤ 14.500 g (0.0405 mol) of disodium hydrogen phosphate dodecahydrate, 43.875 g (0.75 mol) of sodium chloride, and 1.495 g (0.00958 mol) of sodium dihydrogen phosphate dehydrate were weighed and dissolved with double distilled water and the volume was diluted to 5.0 L to obtain phosphate buffer solution (PBS) with the pH of 7.2~7.4.

⑥ 25 g of $Na_2CO_3$ solid powder was dissolved in purified water and diluted to 5 L, the pH was adjusted to 12.00±0.01 with 2N NaOH aqueous solution to prepare alkaline dialysate.

⑦ 0.320 g of bovine serum albumin was weighed and dissolved in 16 ml of PBS in step ⑤ to obtain a bovine serum albumin solution with a concentration of 20 mg/ml.

⑧ Under rapid stirring, the supernatant of step ④ was slowly dropped into the bovine serum albumin solution of the previous step. The volume ratio of the supernatant to the bovine serum albumin solution was 1:5, and the resulting mixture was left to stand overnight at 4° C. to obtain an artificial antigen mixture.

⑨ The artificial antigen mixture from the previous step was transferred to the dialysis bag, dialyzed with the alkaline dialysis solution of step ⑥ for two days, once a day, and then the dialysis bag was transferred to the PBS buffer obtained in ⑤ for 7 times of dialyses, every two time intervals were not less than two hours. After the dialyses was completed, the supernatant was centrifuged to obtain the artificial antigen IV.

Comparative Example 2

The preparation method of the pregabalin artificial antigen of this Comparative Example (the reaction process is shown in FIG. 8) includes the following steps:

(1) Preparation of pregabalin artificial hapten:

① 200 mg (1.258 mmol) of pregabalin was weighed and put into a 50 ml single-necked round bottom flask; 10 ml methanol and 0.5 ml concentrated sulfuric acid was added in with a stir bar, and they were placed into an oil bath at 68° C. with stirring and reflux for 24 hours; after the reaction was complete, they were cooled to room temperature, and $NaHCO_3$ solid was slowly added to the reaction system to adjust the pH to 7-8; the residue was evaporated under reduced pressure, and then was extracted with 15 ml of tetrahydrofuran, filtered and spin-dried to obtain 202 mg (1.168 mmol) of yellowish oily product A;

② 202 mg (1.168 mmol) of the yellowish oily product A of step ① was dissolved in 5 ml of N,N-dimethylformamide (DMF) and placed in a 50 ml three-necked round-bottom flask. The middle mouth was connected to a condenser and dried with anhydrous CaCl2 and the left port of the tube was filled with nitrogen, the right port was plugged with a rubber stopper, 54 mg (1.350 mmol) of NaH (60% mass fraction) solid was added from the right port, and the reaction flask was placed in a 60° C. oil bath and stirred for reaction for 30 minutes, a mixed solution of 368 μL (1.752 mmol) of tert-butyl bromoacetate and 2 ml of N,N-dimethylformamide were added dropwise with a syringe, and continued to react at 60° C. for 17 hours;

after completion of the reaction, the reaction mixture was cooled to room temperature and transferred to a 50 ml single-necked round bottom flask with DMF, then the solvent of the reaction solution was evaporated to dryness under reduced pressure to obtain a yellow viscous substance, then 15 ml of water was added into the flask; then extracted with 15 ml*2 ethyl acetate, the organic phases were combined to one, and washed with 20 ml purified water and 20 ml saturated brine separately, the organic phase was taken and dried with anhydrous $Na_2SO_4$, filtered, and then evaporated to dryness under reduced pressure to obtain 293 mg (0.854 mmol) of brownish-yellow oily substance B.

③ The 293 mg (0.854 mmol) of brownish-yellow oily substance B was dissolved in 15 ml of dichloromethane and 5 ml of trifluoroacetic acid, rapidly stirring for reaction at 25° C. for 5 hours; after the reaction was over, the solvent was evaporated under reduced pressure, then 10 ml of 10% potassium carbonate solution was added, then the aqueous phase was washed with 15 ml*3 of ethyl acetate; the aqueous phase was collected, the pH was adjusted to 3 with 6N hydrochloric acid, and then extracted with 20 ml*3 ethyl acetate; the organic phase was collected, dried with anhydrous magnesium sulfate, filtered, and evaporated to dryness under reduced pressure to obtain a reddish-brown oily product;

The reddish-brown oily product was separated by TLC, the solvent and eluent were absolute ethanol, and the molar ratio of the TLC chromatography solution was 95% ethanol:dichloromethane:1,4-dioxane:ammonia water=8:10:1:1, and the points with $R_f$=0.1~0.5 were collected, eluted with 150 ml absolute ethanol, filtered and concentrated to obtain 82 mg (0.286 mmol) of brown oily product, namely pregabalin artificial hapten V.

(3) Preparation of pregabalin artificial antigen:
④ 82 mg (0.286 mmol) of pregabalin artificial hapten V was placed in a 50 ml round bottom flask, 4.10 ml of N,N-dimethylformamide (DMF) was added, and then 49 mg (0.429 mmol) of N-Hydroxysuccinimide (NHS) and 88 mg (0.429 mmol) of dicyclohexylcarbodiimide (DCC) were added, stirring for reaction at 25° C. overnight, centrifuged after the reaction, and took the supernatant for use.

⑤ 14.500 g of disodium hydrogen phosphate dodecahydrate, 43.875 g of sodium chloride, and 1.495 g of sodium dihydrogen phosphate dehydrate were weighed and dissolved with double distilled water and diluted to 5.0 L to obtain a phosphate buffer solution (PBS) with the pH being 7.2~7.4.

⑥ 25 g of $Na_2CO_3$ solid powder was dissolved in purified water and diluted to 5 L, adjusted pH to 12.00±0.01 with 2N NaOH aqueous solution to prepare alkaline dialysate.

⑦ 0.420 g of bovine serum albumin was weighed and dissolved in 21 ml of PBS in step ⑤ to obtain a bovine serum albumin solution with a concentration of 20 mg/ml.

⑧ Under rapid stirring, the supernatant of step ④ was slowly dropped into the bovine serum albumin solution of the previous step. The volume ratio of the supernatant to the bovine serum albumin solution was 1:5, and the resulting mixture was left to stand overnight at 4° C. to obtain an artificial antigen mixture.

⑨ The artificial antigen mixture from the previous step was transferred to the dialysis bag, dialyzed with the alkaline dialysis solution of step ⑥ for two days, once a day, and then the dialysis bag was transferred to the PBS buffer obtained in ⑤ for 7 times of dialyses, every two time intervals were not less than two hours. After the dialyses was completed, the supernatant was centrifuged to obtain the artificial antigen VI.

Comparative Example 3

The preparation method of the pregabalin artificial antigen of this Comparative Example (the reaction process is shown in FIG. 9) includes the following steps:
(1) Preparation of pregabalin artificial hapten:
① 100 mg (0.628 mmol) of pregabalin was weighed and put into a 50 ml single-necked round bottom flask; 2 ml of 3 A molecular sieve dried benzene and a stir bar were added, and the reaction flask was placed into an ice bath at 0° C., stirred to dissolve, 0.133 ml (0.942 mmol) of trifluoroacetic anhydride was slowly added dropwise to the above reaction solution, then the ice bath was removed, stirring for 1 hrs at room temperature, then the reaction flask was transferred to an oil bath at 78° C. with stirring and reflux for 3 hrs;

after the reaction was over, the reaction mixture was cooled to room temperature; the stir bar was washed with 2 ml of benzene; then the solvent of the reaction solution was evaporated to dryness under reduced pressure to obtain 152 mg (0.596 mmol) of yellowish oily product, namely pregabalin artificial hapten VII. TLC detection showed that the raw material points and product points were not colored under 254 nm ultraviolet light.

(2) Preparation of pregabalin artificial antigen:
② 152 mg (0.596 mmol) of pregabalin artificial hapten VII was dissolved in 7.6 ml of N,N-dimethylformamide (DMF), and then 93 mg (0.805 mmol) of N-Hydroxysuccinimide (NHS) and 166 mg (0.805 mmol) of dicyclohexylcarbodiimide (DCC) were added, stirring for reaction at 25° C. overnight, centrifuged after the reaction, and the supernatant was taken for later use.

③ 14.500 g of disodium hydrogen phosphate dodecahydrate, 43.875 g of sodium chloride, and 1.495 g of sodium dihydrogen phosphate dehydrate were weighed and dissolved with double distilled water and diluted to 5.0 L to obtain a phosphate buffer solution (PBS) with the pH being 7.2~7.4.

④ 25 g of $Na_2CO_3$ solid powder was dissolved in purified water and diluted to 5 L, adjusted pH to 12.00±0.01 with 2N NaOH aqueous solution to prepare alkaline dialysate.

⑤ 0.19 g of bovine serum albumin was weighed and dissolved in 21 ml of PBS in step ⑤ to obtain a bovine serum albumin solution with a concentration of 20 mg/ml.

⑥ Under rapid stirring, the supernatant of step ② was slowly dropped into the bovine serum albumin solution of the previous step. The volume ratio of the supernatant to the bovine serum albumin solution was 1:5, and the resulting mixture was left to stand overnight at 4° C. to obtain an artificial antigen mixture.

⑦ The artificial antigen mixture from the previous step was transferred to the dialysis bag, dialyzed with the alkaline dialysis solution of step ⑥ for two days, once a day, and then the dialysis bag was transferred to the PBS buffer obtained in ⑤ for 7 times of dialyses, every two time intervals were not less than two hours. After the dialyses was completed, the supernatant was centrifuged to obtain the artificial antigen VIII.

Comparative Example 4

The preparation method of the pregabalin artificial antigen of this Comparative Example (the reaction process is shown in FIG. 10) includes the following steps:
(1) Preparation of pregabalin artificial hapten:
① 100 mg (0.628 mmol) of pregabalin was weighed and put into a 50 ml single-necked round bottom flask; 2 ml of 3 A molecular sieve dried benzene and a stir bar were added, and the reaction flask was placed into an ice bath at 0° C., stirred to dissolve, 0.133 ml (0.942 mmol) of trifluoroacetic anhydride was slowly added dropwise to the above reaction solution, then the ice bath was removed, stirring for 1 hrs at room temperature, then the reaction flask was transferred to an oil bath at 78° C. with stirring and reflux for 3 hrs;

after the reaction was over, the reaction mixture was cooled to room temperature; the stir bar was washed with 2 ml of benzene; then the solvent of the reaction solution was evaporated to dryness under reduced pressure to obtain 159 mg (0.624 mmol) of yellowish oily product, namely pregabalin artificial hapten VII. TLC detection showed that the raw material points and product points were not colored under 254 nm ultraviolet light.

②  159 mg (0.624 mmol) of yellowish oily product VII was dissolved in 15 ml of N,N-dimethylformamide (DMF), and then 108 mg (0.936 mmol) of N-Hydroxysuccinimide (NHS) and 179 mg (0.936 mmol) of dicyclohexylcarbodiimide (DCC) were added, stirring for reaction at 26° C. for 20 hours.

after the reaction was over, the reaction solution was transferred to a 60 ml separatory funnel, and washed with 15 ml of 0.1N hydrochloric acid, 15 ml of double distilled water, 15 ml of saturated NaHCO₃ solution and 15 ml of saturated brine in sequence, and the organic phase was dried with anhydrous magnesium sulfate, filtered, and turning to dryness to obtain 198 mg (0.563 mmol) of yellow oily product D;

③ 111 mg (0.732 mmol) of 4-(Methylamino)benzoic acid was dissolved in a mixture of 3 ml of double-distilled water and 12 ml of tetrahydrofuran to obtain a 4-(Methylamino)benzoic acid solution for use; 198 mg (0.563 mmol) of yellow oily product D was dissolved In 6 ml of tetrahydrofuran, the product D solution was obtained; the p-methylaminobenzoic acid solution was added dropwise to the stirring product D solution, and then 1.1 ml of 1N NaOH aqueous solution was added. At this time, the solution pH=10, and the reaction was stirred at 26° C. for 4 hours;

after the reaction, 6N hydrochloric acid was added dropwise to adjust pH=6, extracted with 3×15 ml ethyl acetate, the organic phases were combined, dried, filtered, and dried to obtain a pale yellow foamy solid; the pale yellow foamy solid was dissolved in 2 ml of absolute ethanol, purified by TLC to obtain 128 mg (0.330 mmol) of pregabalin artificial hapten IX. The molar ratio of the TLC chromatography solution was 95% ethanol:dichloromethane:1,4-dioxane: ammonia water=8:10:1:1, and the points with $R_f$=0.5 were collected, eluted with 150 ml absolute ethanol, filtered and concentrated to obtain a product, namely pregabalin artificial hapten IX.

(2) Preparation of pregabalin artificial antigen:

④ 128 mg (0.330 mmol) of pregabalin artificial hapten IX was dissolved in 6.4 ml of N,N-dimethylformamide (DMF), and then 51 mg (0.446 mmol) of N-Hydroxysuccinimide (NHS) and 92 mg (0.446 mmol) of dicyclohexylcarbodiimide (DCC) were added, stirring for reaction at 25° C. overnight, centrifuged after the reaction, and the supernatant was taken for later use.

⑤ 14.500 g of disodium hydrogen phosphate dodecahydrate, 43.875 g of sodium chloride, and 1.495 g of sodium dihydrogen phosphate dehydrate were weighed and dissolved with double distilled water and diluted to 5.0 L to obtain a phosphate buffer solution (PBS) with the pH being 7.2~7.4.

⑥ 25 g of Na₂CO₃ solid powder was dissolved in purified water and diluted to 5 L, adjusted pH to 12.00±0.01 with 2N NaOH aqueous solution to prepare alkaline dialysate.

⑦ 0.16 g of bovine serum albumin was weighed and dissolved in 21 ml of PBS in step ⑤ to obtain a bovine serum albumin solution with a concentration of 20 mg/ml.

⑧ Under rapid stirring, the supernatant of step ④ was slowly dropped into the bovine serum albumin solution of the previous step. The volume ratio of the supernatant to the bovine serum albumin solution was 1:5, and the resulting mixture was left to stand overnight at 4° C. to obtain an artificial antigen mixture.

⑨ The artificial antigen mixture from the previous step was transferred to the dialysis bag, dialyzed with the alkaline dialysis solution of step ⑥ for two days, once a day, and then the dialysis bag was transferred to the PBS buffer obtained in ⑤ for 7 times of dialyses, every two time intervals were not less than two hours. After the dialyses was completed, the supernatant was centrifuged to obtain the artificial antigen X.

Test Example 1

Performance Determination of Pregabalin Artificial Antigens II, IV, VI, VIII, X (1) Identification of pregabalin artificial antigen:

Determination of molar absorption coefficient ε: pregabalin artificial hapten solutions with concentrations of 0 μg/ml, 5 μg/ml, 10 μg/ml, 20 μg/ml, 30 μg/ml, and 40 μg/ml were prepared with the PBS of step ⑤. The scan chart showed that the maximum absorption wavelength of the pregabalin hapten was 270 nm, and the absorbance values were measured at 270 nm, and each concentration was made in parallel. The formula for calculating the molar absorption coefficient (that is, the molar absorption coefficient) is: ε=absorbance/molar concentration.

Determination of conjugate protein concentration: 1 ml of bovine serum protein solution at concentrations of 0 μg/ml, 10 μg/ml, 20 μg/ml, 30 μg/ml, 40 μg/ml, 60 μg/ml, 80 μg/ml, 100 μg/ml, 120 μg/ml were prepared with PBS, 3 ml Coomassie Brilliant Blue staining solution was added, mixed immediately, heated in a water bath at 30° C. for 5 minutes; parallel samples for each concentration was made, the absorbance values were measured at 655 nm, and the relationship curve between the protein concentration and the absorbance was drawn. The artificial antigen solution (prepared with PBS) were diluted in a certain proportion, the absorbance values of the artificial antigen were measured at 655 nm, and the corresponding protein concentration values of the artificial antigen solution from the curve were read.

Coupling ratio determination: 100 μg/ml bovine serum albumin in PBS was prepared, the conjugate (ie pregabalin artificial antigen) was diluted with PBS to 100 μg/ml, the absorbance value A1 was measured at 292 nm; PBS was used as the blank solution, and the absorbance value A2 was measured; the coupling ratio γ is: γ=[(A1−A2)/ε]/(100×10−3/65000).

Wherein ε is the molar absorption coefficient (L/mol), 65000 is the molecular weight of bovine serum albumin, and 100×10−3 is the concentration of bovine serum albumin (μg/ml).

When using bovine gamma globulin as a carrier, the coupling ratio is calculated as: γ=[(A1−A2)/ε]/(100×10−3/150000); among them, 150,000 is the molecular weight of bovine gamma globulin.

TABLE 1

Coupling ratio and molar absorption coefficient
of each pregabalin artificial antigen

| Number | Artificial antigen | Coupling ratio | Conjugate protein concentration | Molar absorption coefficient |
|---|---|---|---|---|
| Embodiment 1 | II | 21 | 11.32 mg/ml | 5134.25 |
| Comparative Example 1 | IV | 17 | 12.60 mg/ml | 5328.46 |
| Comparative Example 2 | VI | 20 | 15.35 mg/ml | 4678.23 |
| Comparative Example 3 | VIII | 19 | 2.95 mg/ml | 4721.16 |
| Comparative Example 4 | X | 26 | 3.17 mg/ml | 5812.44 |

It can be seen from TABLE 1 that the structure of the artificial hapten has a great influence on the binding ratio when the artificial hapten is coupled to the carrier protein.

(2) Animal immunity

Pregabalin artificial antigens II, IV, VI, VIII, X were immunized with New Zealand white rabbits, and the obtained immune serum were tested for their titers by ELISA method. The test results were shown in TABLE 2.

TABLE 2

Titer test results of each immune serum

| Number | Pregabalin artificial antigen | Titer of immune serum |
|---|---|---|
| Embodiment 1 | II | 90000 |
| Comparative Example 1 | IV | 20000 |
| Comparative Example 2 | VI | 30000 |
| Comparative Example 3 | VIII | 76000 |
| Comparative Example 4 | X | 50000 |

It can be seen from TABLE 2 that compared with Embodiment 1 and Comparative Example 3, the titers of the immune serum obtained by using the pregabalin artificial antigen of each Comparative Example for animal immunization are all low and cannot be used in immunoassays. The immune serum obtained by using artificial antigens of pregabalin II and VIII for animal immunization has titers of 1:90000 and 76,000, respectively, which can be used in immunoassays and can provide a more convenient, rapid and accurate way for the detection of pregabalin.

Regarding Embodiment 1 and Comparative Example 3, it is still necessary to further explore whether different carrier proteins and different coupling methods can improve the performance of the antigen. Therefore, Comparative Example 5 to Comparative Example 10 were implemented.

Comparative Example 5

The preparation method of the pregabalin artificial antigen of this Comparative Example (the reaction process is shown in FIG. 11) includes the following steps:
(1) Preparation of pregabalin artificial hapten:
①-② Same as Embodiment 1.
(2) Preparation of pregabalin artificial antigen:
③-⑧ Similar to Embodiment 1, the bovine serum albumin was replaced with bovine gamma globulin as the carrier, and the pregabalin artificial hapten I was coupled to obtain the pregabalin artificial antigen XI.

Comparative Example 6

The preparation method of the pregabalin artificial antigen of this Comparative Example (the reaction process is shown in FIG. 12) includes the following steps:
(1) Preparation of pregabalin artificial hapten:
①-② Same as Embodiment 1.
(2) Preparation of pregabalin artificial antigen:
③ 72 mg (0.266 mmol) of pregabalin artificial hapten I was weighed and placed in a 50 ml round bottom flask, 4 ml of N,N-dimethylformamide (DMF) was added, followed by 37 µL (0.266 mmol) of triethylamine and 34 µL (0.266 mmol) Isobutyl chloroformate; stirring for reaction for 18 hours at room temperature, centrifuged after the reaction, and the supernatant was taken for later use.
④-⑧ Same as Embodiment 1, to obtain pregabalin artificial antigen XII.

Comparative Example 7

The preparation method of the pregabalin artificial antigen of this Comparative Example (the reaction process is shown in FIG. 13) includes the following steps:
(1) Preparation of pregabalin artificial hapten:
①-② Same as Embodiment 1.
(2) Preparation of pregabalin artificial antigen:
③ Same as Comparative Example 6
④-⑧ Similar to Comparative Example 6, except that bovine serum albumin was replaced with bovine gamma globulin to couple with pregabalin artificial hapten I to obtain pregabalin artificial antigen XIII.

Comparative Example 8

The preparation method of the pregabalin artificial antigen of this Comparative Example (the reaction process is shown in FIG. 14) includes the following steps:
(1) Preparation of pregabalin artificial hapten:
① Same as Comparative Example 3.
(2) Preparation of pregabalin artificial antigen:
②-⑧ Similar to Comparative Example 6, except that bovine serum albumin was replaced with bovine gamma globulin to couple with pregabalin artificial hapten VII to obtain pregabalin artificial antigen XIV.

Comparative Example 9

The preparation method of the pregabalin artificial antigen of this Comparative Example (the reaction process was shown in FIG. 14) includes the following steps:
(1) Preparation of pregabalin artificial hapten:
① Same as Comparative Example 3.
(2) Preparation of pregabalin artificial antigen:
② 152 mg (0.596 mmol) of pregabalin artificial hapten VII was weighed and placed in a 50 ml round bottom flask, 7.6 ml of N,N-dimethylformamide (DMF) was added, followed by 83 µL (0.596 mmol) of triethylamine and 76 µL (0.596 mmol) Isobutyl chloroformate; stirring for reaction for 18 hours at room temperature, centrifuged after the reaction, and the supernatant was taken for later use.
③-⑦ Same as Comparative Example 3, to obtain pregabalin artificial antigen XV.

Comparative Example 10

The preparation method of the pregabalin artificial antigen of this Comparative Example (the reaction process was shown in FIG. 15) includes the following steps:

(1) Preparation of pregabalin artificial hapten:
1 Same as Comparative Example 3.
(2) Preparation of pregabalin artificial antigen:
2 152 mg (0.596 mmol) of pregabalin artificial hapten VII was weighed and placed in a 50 ml round bottom flask, 7.6 ml of N,N-dimethylformamide (DMF) was added, followed by 83 μL (0.596 mmol) of triethylamine and 76 μL (0.596 mmol) Isobutyl chloroformate; stirring for reaction for 18 hours at room temperature, centrifuged after the reaction, and the supernatant was taken for later use.
3-7 Similar to Comparative Example 3, except that bovine serum albumin was replaced with bovine gamma globulin to couple with pregabalin artificial hapten VII to obtain pregabalin artificial antigen XVI.

Test Example 2

Performance Determination of Pregabalin Artificial Antigens XI, XII, XIII, XIV, XV, XVI (1) According to the method of Test example 1, the coupling ratios and concentrations of pregabalin artificial antigens XI, XII, XIII, XIV, XV, XVI were measured. See TABLE 3.

TABLE 3

Coupling ratio and concentration of each pregabalin artificial antigen

| Number | Artificial antigen | Coupling ratio | Conjugate protein concentration | Molar absorption coefficient |
|---|---|---|---|---|
| Embodiment 1 | II | 21 | 11.32 mg/ml | 5134.25 |
| Comparative Example 5 | XI | 19 | 14.18 mg/ml | 5134.25 |
| Comparative Example 6 | XII | 27 | 12.67 mg/ml | 5134.25 |
| Comparative Example 7 | XIII | 12 | 10.17 mg/ml | 5134.25 |
| Comparative Example 8 | VIII | 19 | 2.95 mg/ml | 4721.16 |
| Comparative Example 9 | XIV | 29 | 2.16 mg/ml | 4721.16 |
| Comparative Example 10 | XV | 27 | 3.38 mg/ml | 4721.16 |
| Comparative Example 11 | XVI | 21 | 3.07 mg/ml | 4721.16 |

(2) Animal immunity
Pregabalin artificial antigens XI, XII, XIII, XIV, XV, XVI were immunized with New Zealand white rabbits, and the obtained immune serum were tested for their titers by ELISA method. The test results were shown in TABLE 4.

TABLE 4

Titer test results of each immune serum

| Number | Pregabalin artificial antigen | Titer of immune serum |
|---|---|---|
| Embodiment 1 | II | 90000 |
| Comparative Example 5 | XI | 70000 |
| Comparative Example 6 | XII | 45000 |
| Comparative Example 7 | XIII | 55000 |
| Comparative Example 8 | VIII | 76000 |
| Comparative Example 9 | XIV | 65000 |
| Comparative Example 10 | XV | 60000 |
| Comparative Example 11 | XVI | 30000 |

It can be seen from TABLE 4 that the artificial antigen II obtained in Embodiment 1 had the highest titer of the immune serum obtained from animal immunization, and was better than the titer of the immune serum corresponding to the artificial antigen VIII. And the polyclonal antibody obtained by combining with the artificial antigen II can achieve better results and can be better used for immunoassays. It can provide a more convenient and rapid way for the detection of pregabalin.

What is claimed is:
1. A pregabalin artificial antigen, having a molecular structure formula as shown in (II):

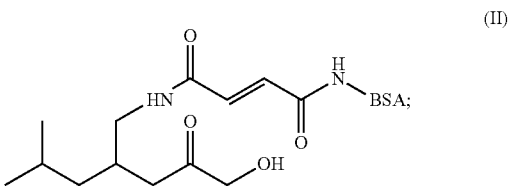

(II)

wherein BSA is bovine serum albumin.

2. A method for preparing the pregabalin artificial antigen as claimed in claim 1, comprising steps of:
(1) dissolving pregabalin in methanol, adding concentrated sulfuric acid, stirring to react at 68° C. for 24 hours to obtain a first reaction product, then the first reaction product is subjected to alkalization, evaporating, and extraction to obtain a yellowish oily product A;
(2) mixing the obtained yellowish oily product A with maleic anhydride in a molar ratio of 1:2-3 in dichloromethane, stirring to react at room temperature for 20 hours to obtain a second reaction product, then the second reaction product is washed, dried, filtered, dried, and then subjected to thin-layer chromatography to obtain a light yellow oily product, namely pregabalin artificial hapten I;

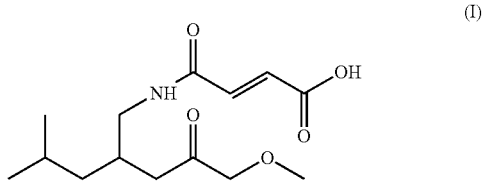 [SMILES: COCC(=O)CC(CNC(=O)/C=C/C(=O)O)CC(C)C]

(I)

(3) combining the pregabalin artificial hapten I with bovine serum albumin by an active ester method to obtain the pregabalin artificial antigen II as claimed in claim 1.
3. The method for preparing the pregabalin artificial antigen according to claim 2, comprising steps of:
(a) mixing the pregabalin artificial hapten, N-hydroxysuccinimide, and dicyclohexylcarbodiimide in a molar ratio of 1:1.35-1.5:1.35-1.5 in N,N-Dimethylformamide, stirring to react at 25° C. for 18 hours; centrifugating and collecting a first supernatant;
(b) adding the first supernatant dropwise to a bovine serum albumin solution to obtain a reaction mixture, allowing the reaction mixture to stand at 4° C. overnight, dialyzing and centrifuging to obtain a second supernatant solution to obtain the pregabalin artificial antigen of claim 1.
4. The method for preparing the pregabalin artificial antigen according to claim 3, wherein in step (b), the concentration of the bovine serum albumin solution is 20 mg/ml, and the volume ratio of the first supernatant to the bovine serum albumin solution is 1:5.

* * * * *